United States Patent [19]

Goudal

[11] 4,092,129
[45] May 30, 1978

[54] PROCESS FOR PRODUCING METHANE RICH GAS

[75] Inventor: Philippe Goudal, Bures sur Yvette, France

[73] Assignee: Electricite de France (Service National), Paris, France

[21] Appl. No.: 716,627

[22] Filed: Aug. 23, 1976

[30] Foreign Application Priority Data

Aug. 26, 1975 France .................. 75 26262

[51] Int. Cl.² .......................... C10J 3/18; C10K 3/04
[52] U.S. Cl. ...................................... 48/210; 204/129; 260/449 M
[58] Field of Search ................. 48/65, 197 R, 210; 260/449 M; 423/415 A, 439; 204/129, 277, 278; 11/DIG. 6; 166/260

[56] References Cited

U.S. PATENT DOCUMENTS

| | | | |
|---|---|---|---|
| 1,865,053 | 6/1932 | Woodruff | 423/415 A |
| 2,804,146 | 8/1957 | Crawford | 166/260 |
| 3,325,253 | 6/1967 | Schmidt | 423/415 A |
| 3,556,749 | 1/1971 | Spacil | 48/197 R X |
| 3,577,329 | 5/1971 | Shalit | 204/129 X |
| 3,619,365 | 11/1971 | Boguley et al. | 260/449 M |
| 3,852,180 | 12/1974 | Gregory | 260/449 M X |

FOREIGN PATENT DOCUMENTS 2,503,367 9/1976 Germany .................. 260/449 M

Primary Examiner—S. Leon Bashore
Assistant Examiner—Peter F. Kratz
Attorney, Agent, or Firm—Pollock, Vande Sande & Priddy

[57] ABSTRACT

Production of gas rich in methane employing an electrolytic cell whereby oxygen is produced at the anode and hydrogen is produced at the cathode thereof. The cell includes a post-anodic compartment containing coal and/or lignite for reacting with the oxygen to produce CO. The CO in turn is reacted with the hydrogen from the cathode to produce the gas rich in methane.

6 Claims, 1 Drawing Figure

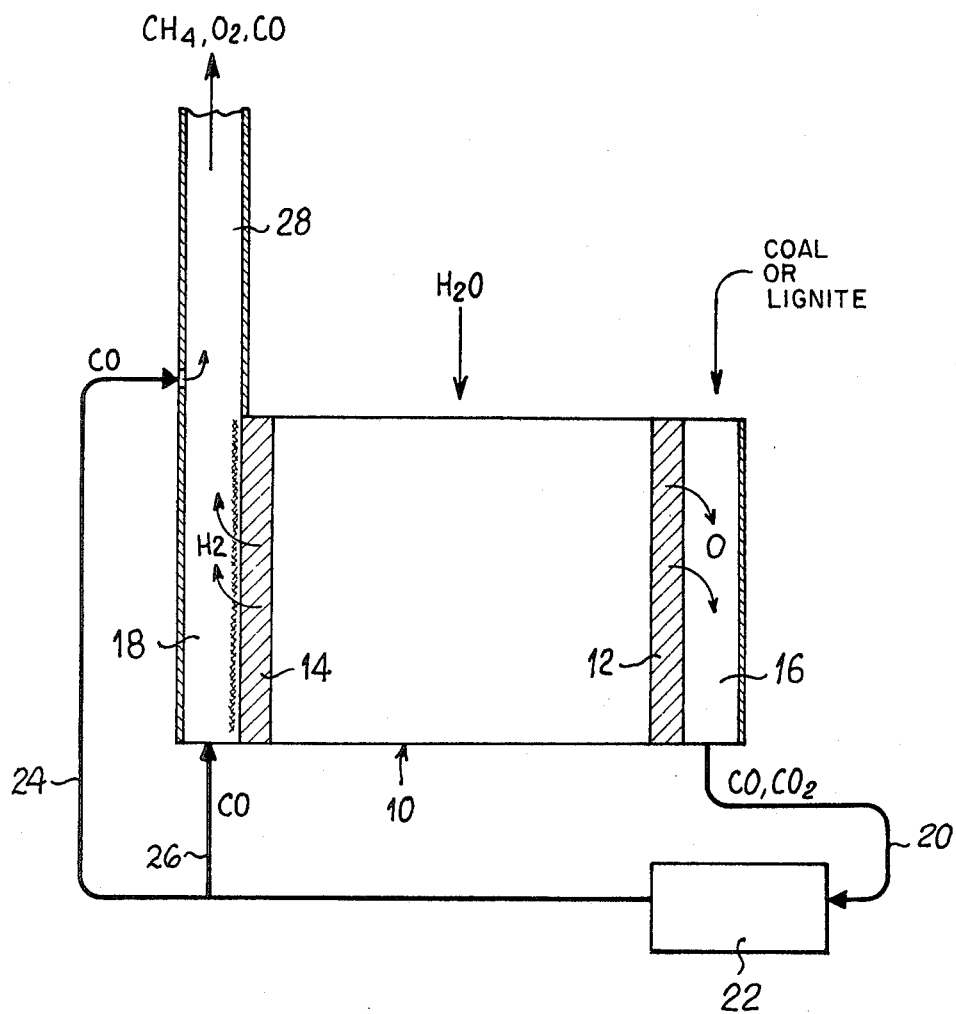

PROCESS FOR PRODUCING METHANE RICH GAS

The present invention concerns the production of energy for domestic and industrial needs.

The recent trend in the energy field goes towards the production of energy essentially as electricity since this allows all kinds of end-uses; mechanical, thermal or chemical; and facilitates transportation because it can be distributed everywhere.

However electrical energy has the disadvantage of not being storable and consequently requiring variable production following the hours of the day and the days of the week or year because the demand for electrical energy is very variable with time.

It has now become apparent that certain energy demands, and especially demands for thermal energy, could be met with advantage by using gaseous fuel if produced in an economical fashion. This is so since a gaseous fuel can be easily transported and distributed like electricity, but furthermore it has the advantage of being storable for taking into account fluctuations in demand.

Natural gas meets this need and is exploited on a large scale for domestic and industrial heating.

It is however necessary to provide a substitute product to meet a growing demand for this type of energy.

In this respect methane is a fuel gas which may be an excellent energy carrier since its calorific value is high, and moreover its use does not require substantial modification of the equipment and techniques already available for using natural gas.

It has already been proposed to produce methane as an energy carrier in coal or lignite installations by carrying out gasification of coal in the presence of steam. The combustion of the coal liberates thermal energy required for working of the installation; thus for example part of the coal is simply burnt to raise the temperature and rotate the generating turbines for eventual recovery of electricity, the other part of the coal being raised to high temperatures and gasified so as to particularly produce methane.

This process has the drawback of consuming much energy: the equivalent of more than two nuclear therms for each cubic meter of methane produced.

Furthermore, this process is only of interest if the coal itself is the fuel which provides the heat needed in the gasification reaction occurring at high temperature. It is therefore of interest only in those areas where coal is available at a low cost price, which is not the case in a large number of countries.

It would also be possible to prepare hydrogen by conventional electrolysis, and methane from this hydrogen and coal, but the energy subsequently recoverable by combustion of this methane is much less than the energy required for its production. The energy yield is not better than 40% which is most unfavourable.

In order to improve the production of energy, while foreseeing a principal energy carrier which is methane and thereafter a second energy carrier which will be electricity, and while lowering the cost and increasing production efficiency, the present invention offers an installation for the production of energy from an energy source, which can be a nuclear fuel, this installation having a means of production of electrical energy and a cell for reactive electrolysis to produce a gas rich in methane, this cell using as fuel electricity being all or part of the energy given out by the means of production of electrical energy. The definition of reactive electrolysis will be given below.

The principal energy carrier provided by the installation is thus a gas which is methane, which is storable. A second carrier is electricity if it is desired to produce a surplus above that strictly required for the reactive electrolysis in the cell. Moreover, it is possible, for example, to produce electricity during the peak hours and be satisfied with producing methane during the slack hours.

By "reactive electrolysis" is herein meant an electrolysis whose products are subjected to a chemical reaction immediately after their appearance at an electrode. This reaction has as an object to transform at least one of the products in order to eliminate it as the electrolysis proceeds, and thus to lower the products partial pressure or more generally its thermodynamic activity (abbreviated in the following: activity) at the electrodes in such a way that the efficiency of the electrolysis is particularly enhanced.

The thermal energy yield of gas rich in methane produced in such an installation is of the order of 2. In other words, the thermal energy which can be recovered by combustion of a cubic meter of this gas is about twice that needed to produce the cubic meter. This value is thus of much more interest than obtained by processes used up until now in installations for production of energy, and this is why the installation according to the invention is of special note.

Two reactive electrolysis processes are more particularly attractive.

The first consists in causing oxygen given off at the anode of the reactive electrolysis cell to react with powdered coal in the presence of an appropriate catalyst to give the reaction $C + O \rightarrow CO$ (the oxygen supposedly being formed at the vicinity of the anode, but this is not essential), with possible formation of $CO_2$ because reaction must take place at low temperature (350° C in the gas).

Carbon monoxide produced is then reacted with the hydrogen formed at the cathode, either reactively or outside the cell, to give a mixture of methane, oxygen and water according to the reactions $CO + 3H_2 \rightarrow CH_4 + H_2O$, $CO + 2H_2 \rightarrow CH_4 + \frac{1}{2}O_2$ and $2CO + 2H_2 \rightarrow CH_4 + CO_2$, the first being the principal as its speed is much greater than that of the others, the more so because it can be catalysed for example by a sulphide of molydenum or chromium.

This mixture, with furthermore the surplus of carbon monoxide produced at the anode, comprises gas rich in methane serving as the energy carrier distributed to the users, but the methane can equally be separated if desired.

The second type of reactive electrolysis which can be employed for production of gas rich in methane consists in reacting a fluidized bed of coal (or lignite) with the oxygen of the anode so as to obtain not only carbon monoxide CO but also some carbon dioxide gas $CO_2$ which can itself react further with coal to produce carbon monoxide according to the reaction $CO_2 + C \rightarrow 2CO$.

A part of the CO is returned to the cathode for methanation $(CO + 3H_2 \rightarrow CH_4 + H_2O)$. The rest is surplus and can remain as a fraction of poor gas (less energy) in the methane mix. The corresponding over-concentration will help the methanation reaction, in accordance with the law of mass action.

It is to be noted that CO or $CO_2$ can be stored, which permits allowance to be made for variations in the energy demand and which means the present process has versatility.

The various characteristics of an installation according to the invention for production of energy will now be described.

Preferably the installation operates with a nuclear fuel.

The heat produced by this fuel serves to heat steam which turns in a known manner a series of turbines in order to produce electricity, and supply one or more reactive electrolysis cells.

This cell essentially contains an aqueous solution, e.g. potassium sulphate or potassium bisulphate ($KHSO_4$) to facilitate obtaining a release of oxygen at the anode and hydrogen at the cathode.

In known manner the anode and cathode employed are in porous form to allow immediate chemical reaction with the gasses evolved during the electrolysis. On the anode side it is preferred to circulate a fluid bed of coal or lignite.

The oxygen evolved at the anode passes therethrough and reacts with the fluidized bed of coal to give carbon monoxide CO: $C + O \rightarrow CO$, and possibly carbon dioxide gas $CO_2$.

This reaction is accompanied by a notable evolution of heat (26.4 kcal per mole of CO formed) which thus acts in the electrolytic cell as a source of heat, though the elevation of the temperature in the cell is limited to about 400° C by the use of an appropriate catalyst which promotes the above reaction at this relatively low temperature. In fact, it is not desirable to raise the temperature of the electrolytic cell too much since it would require special construction to allow this temperature.

One catalyst which allows the reaction $C + O \rightarrow CO$ to proceed in a practical and quantatative fashion at 400° C with naiscent oxygen is carbon tetrachloride. Other chlorinated products such as carbon oxychloride and $COCl_2$ can be equally suitable.

This reactive electrolysis at the anode allows lowering of the electrolytic potential. Indeed, this potential will be about 1.05 volt for a non-reactive reversible electrolysis (at 400° C), and one can expect to lower this to less than 0.6 volts or even 0.2 volts by sufficiently decreasing the partial pressure of oxygen at the electrode. It is of interest to provide for recovery, as for example in the form of electricity, of the heat liberatd in the electrolytic cell by the post-anodic reaction ($C + O \rightarrow CO$).

It is possible to recover as electricity about 30% of the thermal energy given off, by conversion in a turbine at low temperature (400° C). It is possible to obtain a recovery of 0.01 kwh in the form of electricity per mole of CO formed.

Now, electrolysis of a mole of water consumes about 0.04 kwh with a potential difference of 0.6 volts at the electrode boundaries, and still less if the potential difference is less. The recovery of 0.01 kwh per mole is thus of actual interest for realistically improving the global output of electrolysis.

It is possible to foresee a turbo-generator group (for example with ammoniac) capable of recovering energy at low temperature (400° C) and of converting it to electrical energy.

The installation includes a circuit for treatment and directing, towards the cathode, of the carbon monoxide produced at the anode. This treatment consists of heating carbon moxoxide in the presence of catalyst to decompose the carbon dioxide gas which it possibly contains.

The cathode is preferably porous like the anode to permit reaction of the carbon monoxide which circulates on one side with the hydrogen given off by electrolysis at the other side.

The reaction is the following:

$$CO + 3H_2 \rightarrow CH_4 + H_2O$$

It takes place the more easily if the carbon monoxide is pure and especially if it contains less sulphur. A desulphurization device (by passage over lime-stone) is preferably provided at the exit of the post-anodic compartment.

The above reaction lowers the partial pressure of the hydrogen by consuming it as it is formed at the cathode, and the efficiency of the electrolysis is much improved. Nevertheless, the improvement is not as noticeable as at the anode.

The gas produced in this post-cathodic reaction is a mixture rich in methane; it contains oxygen as well as methane, and also carbon oxide CO since for 2 moles of water electrolysed, 2 moles of CO are produced in the post-anodic reaction but 2 mole at most serve to form the methane by the post-cathodic reaction.

However, if a small amount of carbon dioxide gas is formed, particularly in the post-anodic reaction where it is possible that there is not exclusive formation of carbon oxide, it is possible to use the heat of the nuclear fuel in the installation to redecompose this carbon dioxide gas in the presence of coal at 800° C (Boudouard's reaction $CO_2 + C \rightarrow 2CO$, quantitative at this temperature).

It is equally to be noted that the reaction $CO + 3H_2 \rightarrow CH_4 + H_2O$ is of interest because it is favoured when there is an excess of CO, which is exactly the case as said above.

Finally, this reaction is more endothermic at high temperature and it is desirable to increase the temperature of the reaction and equally the pressure (since the reaction leads to a marked decrease in volume).

It is desirable to provide a tempering station for rapidly cooling the methane-containing mixture produced (preferably below 300° C) and thus recover the heat contained in this mixture.

If one wants to separate the methane from the other constituents of the mixture, it is possible to do it by, for example, liquefaction of the mixture (which is often liquified for storing).

In brief, the various reactions which are employed in this installation for the production of energy are:

$C + O \rightarrow CO$ at the anode in the presence of catalysis
$CO + 3H_2 \rightarrow CH_4 + H_2O$ for example at the cathode.

In reality, the first reaction does not precede quantitatively at 400° C, in which event the carbon dioxide gas $CO_2$ is likewise produced in variable proportions.

It is even possible to arrange to obtain in practice exclusively the carbon dioxide gas by suppressing all catalysation.

In fact, at 427° C (700° k), it is possible to calculate that $\log P_{CO_2} - \log P_{CO} = 3.57$ (at thermodynamic equilibrium between the constituents C, $O_2$, CO and $CO_2$).

This indicates that the partial pressure of carbon monoxide is about 1500 times less than the partial pressure of the carbon dioxide.

Moreover, it is equally possible to calculate that at this temperature $\log P_{CO_2} - \log P_{O_2} = 12.96$, which indicates that the reaction is practically quantitative and that the oxygen is nearly totally eliminated as soon as it appears at the anode of the electrolytic cell.

In these conditions, this reaction $C + 2O \rightarrow CO_2$ is of more interest because it allows especial increase in the electrolytic efficiency by markedly lowering the partial pressure of oxygen.

This reaction of burning of carbon is moreover strongly exothermic (94 kcal per mole of $CO_2$ formed) and it increases the temperature of the electrolytic cell. It is useful to provide recovery of the energy given off and convert it into electrical energy which one can use for maintaining the cell.

The nuclear installation provides an amount of heat at high temperature (especially from nuclear fuel) and this high temperature allows conversion of the carbon dioxide gas into carbon monoxide in the presence of coal, following the reactions $C + CO_2 \rightarrow 2CO$, or without coal by the reaction $CO_2 \rightarrow CO + \frac{1}{2}O_2$ with a catalyst which can be a phosphate or a borate.

The carbon monoxide is then carried to the cathode of the electrolytic cell to give methane ($CO + 3H_2 \rightarrow CH_4 + H_2O$.)

In brief, two variations of installations in accordance with the invention are possible: the first employs a post-anodic compartment of the electrolytic cell for the reaction $C + O \rightarrow CO$, the second a post-anodic compartment for the reaction $C + 2O \rightarrow CO_2$ then, in a compartment which receives the heat of the nuclear heater the reactions $CO_2 + C \rightarrow 2CO$, or $CO_2 \rightarrow CO + \frac{1}{2}O_2$ and, in two variants, the reaction $CO + 3H_2 \rightarrow CH_4 + H_2O$ produces e.g. in a post-cathodic compartment a gaseous mixture rich in methane ($CH_4$, and $CO$). In practice the two variants can be mixed if the coal is converted at the time to $CO$ and $CO_2$.

A further variation of the installation according to the invention consists in providing circulation of carbon monoxide originating not from oxidation at the anode of a fluidized bed of coal or lignite but from a waste burner.

This carbon monoxide is contacted with naiscent oxygen at the anode of the electrolytic cell to eliminate it and to increase the efficiency of the cell by lowering the partial pressure of oxygen. The carbon dioxide gas $CO_2$ produced ($CO + O \rightarrow CO_2$) is then decomposed at high temperature (obtained from the nuclear boiler) in the presence of coal to regenerate the carbon monoxide ($CO_2 + C \rightarrow 2CO$).

One of the molecules of $CO$ is recycled in the post-anodic compartment, the other is evolved towards the cathode where it takes part in the methanation ($CO + 3H_2 \rightarrow CH_4 + H_2O$).

It is important to declare that the calorific power of the gas rich in methane produced by the installation according to the invention is much above that of coal: the quantity of gas produced by methanation from one ton of coal has a calorific power equal to 1.7 times the calorific power of one ton of carbon, which shows the importance of the production of cheap methane, above all in a country which does not possess much coal.

One can calculate by an example that the consumption of energy to produce the reactions for conversion of carbon dioxide gas into carbon monoxide, and carbon monoxide into methane is about 2.4 therms per cubic meter of methane produced. Moreover, the consumption of electricity for electrolysis may be about 2 nuclear therms or less for two cubic meters of electrolysed steam (thus for 0.66 cubic meters of $CH_4$ produced). In total, the consumption of energy will be 5.4 therms while the subsequent calorific power of the methane produced is 8.55 therms per cubic meter, which shows that the energy amplification coefficient brought about by this process is 8.55/5.4 hence about 1.6.

It is to noted that the correctly expressed methanation reaction ($CO + 3H_2 \rightarrow CH_4 + H_2O$) does not have to be carried out "reactively", i.e. in a post-cathodic compartment to eliminate the hydrogen as soon as it is formed. The reaction can be carried out outside the cell. Against this, reactive electrolysis at the anode is always foreseen.

The process according to the present invention can be put into operation in an installation schematically represented in the single accompanying FIGURE. This FIGURE is not a drawing having dimensions representative of the real thing.

The electrolytic cell 10 has an anode 12 and a cathode 14, both of which consist of layers of sintered nickel surperimposed in the form of a thin nickel laminate united at the sintered layers and pierced by appropriately sized pores (about 50 microns) which are in contact with the electrolyte. These electrodes 12 and 14 are thus porous and permit passage of the hydrogen and oxygen resulting from the electrolysis respectively in a post anodic compartment 16 and a post-cathodic compartment 18.

In the post anodic compartment, and as already explained, either powdered coal (which falls under the influence of gravity) or carbon monoxide is circulated, or as a further alternative the two together, and at the exit is recovered through a conduit 20 a mixture $CO$ and $CO_2$ in variable proportions according to whether more less catalyst is employed to avoid the formation of $CO_2$.

This mixture of $CO$ and $CO_2$ is treated in a treatment device 22 at high temperature (disposed near the nuclear boiler to obtain the heat).

This treatment circuit 22 principally serves to decompose at high temperature the carbon dioxide $CO_2$ to produce a new carbon monoxide $C0$. This oxide, like that already formed is carried by the conduits 24, 26 to various points of the post-cathodic compartment 18 and a final compartment 28 located in the exit of the post-cathodic compartment 18.

In the compartments 18 and 28 the methanation reaction $CO + 3H_2 \rightarrow CH_4 + H_2O$ occurs. As this reaction has a modest rate, a sufficient length for the compartment 28 is provided and it is at the exit of this compartment that the gaseous mixture is recovered which will serve as the storable energy source. A molybdenum sulphide catalyst is applied on the wall of the cathode at the interior of the post cathodic compartment. The electrolyte in the cell 10 between the anode and the cathode is preferably potassium sulphate contained in a porous block of aluminium traversed by canals into which is injected steam at 200° C and at 30 bars. Steam at such temperatures serves to cool the cell to an average temperature of 350° to 400° C.

By way of illustration the dimensions of the cell can be the following: the cell is regular, its height is 2 to 3 meters, the electrodes are separated by distance of 0.5 to 1 cm. The post anodic and post cathodic compartments are several centimeters wide and extend the height of the cell.

The compartment 28 has the same width and equally extends 2 to 3 meters in length.

What I claim is:

1. A process for the production of gas rich in methane, the process comprising the steps of providing an electrolytic cell having an anode and a cathode and containing an aqueous electrolytic solution, electrolyzing said aqueous electrolytic solution to produce oxygen at said anode and hydrogen at said cathode, reacting a carbonaceous fuel selected from the group consisting of coal and lignite at said anode with said oxygen to give carbon monoxide, and reacting said carbon monoxide with said hydrogen according to the reaction $CO + 3H_2 \rightarrow CH_4 + H_2O$.

2. The process of claim 1 wherein said reacting of said carbon monoxide with said hydrogen occurs at said cathode.

3. The process of claim 1 wherein said reacting a carbonaceous fuel selected from the group consisting of coal and lignite at said anode with said oxygen is conducted in a fluidized bed of said carbonaceous fuel.

4. The process of claim 1 wherein said reacting of a carbonaceous fuel is carried out at a temperature of about 400° C in the presence of a catalyst for the principle production of carbon monoxide.

5. The process of claim 4 wherein said catalyst is carbon tetrachloride or carbon oxychloride.

6. A process for the production of gas rich in methane, the process comprising the steps of providing an electrolytic cell having an anode and a cathode and containing an aqueous electrolytic solution, electrolyzing said aqueous electrolytic solution to produce oxygen at said anode and hydrogen at said cathode, reacting carbonaceous fuel selected from the group consisting of coal and lignite at said anode with said oxygen to give carbon dioxide, reacting said carbon dioxide with a carbonaceous fuel to give carbon monoxide, and reacting said carbon monoxide with said hydrogen according to the reaction $CO + 3H_2 \rightarrow CH_4 + H_2O$.

* * * * *